US006577897B1

(12) United States Patent
Shurubura et al.

(10) Patent No.: US 6,577,897 B1
(45) Date of Patent: Jun. 10, 2003

(54) NON-INVASIVE MONITORING OF PHYSIOLOGICAL PARAMETERS

(75) Inventors: Alex Shurubura, Jerusalem (IL); Michael Kosoburd, Jerusalem (IL)

(73) Assignee: Nimeda Ltd., Tel Aviv (IL)

( * ) Notice: Subject to any disclaimer, the term of this patent is extended or adjusted under 35 U.S.C. 154(b) by 0 days.

(21) Appl. No.: 09/719,851

(22) PCT Filed: Apr. 9, 1999

(86) PCT No.: PCT/IL99/00195
§ 371 (c)(1),
(2), (4) Date: Feb. 1, 2001

(87) PCT Pub. No.: WO99/65390

PCT Pub. Date: Dec. 23, 1999

(30) Foreign Application Priority Data

Jun. 17, 1998 (IL) ................................................. 124964

(51) Int. Cl.[7] .................................................. A61B 5/05
(52) U.S. Cl. ...................................................... 600/547
(58) Field of Search .......................... 600/547, 26, 391, 600/300, 544, 545, 347, 368, 372; 607/152; 204/403.04, 403.11, 403.14, 412; 205/777.5, 792; 340/539, 575, 576, 693.5

(56) References Cited

U.S. PATENT DOCUMENTS

| 4,793,362 | A | | 12/1988 | Tedner | |
|---|---|---|---|---|---|
| 5,450,845 | A | | 9/1995 | Axelgaard | |
| 5,465,715 | A | * | 11/1995 | Lyons | 600/391 |
| 5,813,993 | A | * | 9/1998 | Kaplan et al. | 600/26 |
| 5,917,415 | A | * | 6/1999 | Atlas | 600/372 |
| 5,989,409 | A | * | 11/1999 | Kurnik et al. | 600/347 |

FOREIGN PATENT DOCUMENTS

| EP | 0 575 984 | 12/1993 |
|---|---|---|
| WO | 96 35370 | 11/1996 |

* cited by examiner

*Primary Examiner*—Max F. Hindenburg
*Assistant Examiner*—Brian Szmal
(74) *Attorney, Agent, or Firm*—Browdy and Neimark, P.L.L.C.

(57) ABSTRACT

A non-invasive diagnostic physiological monitoring system for mammals, particularly humans is disclosed. The system includes: at least two surface contact electrodes; means for holding the electrodes in contact with an exterior surface of a mammal; means for pairing the electrodes; an electronic block coupled to at least one of the pairings wherein the block includes a transmitter for transmitting a predetermined electrical signal to a first pair of electrodes in the pairing, a and detector for detecting electrical impedance characteristics on the first pair of electrodes or on a second pair of electrodes in the pairing; and a signal processor coupled to the detector wherein the electrical impedance characteristics are divided into at least two groups by frequency.

8 Claims, 1 Drawing Sheet

NON-INVASIVE MONITORING OF PHYSIOLOGICAL PARAMETERS

FIELD OF THE INVENTION

This invention generally relates to a non-invasive diagnostic system for the monitoring of physiological parameters. More specifically the present invention relates to measuring and processing bio-impedance. Furthermore, the present invention relates to a method for disclosing a physiological indication using a bio-impedance measuring system.

BACKGROUND OF THE INVENTION

There are numerous relevant technologies relates to impedance measuring physiological monitoring systems; and to methods of data analysis, particularly useful for extracting physiologically significant detail from impedance measurements. Consideration of such useful data analysis methods has heretofore not been appreciated; especially in that data analysis can be so useful for extracting physiologically significant detail from (prolonged) impedance measurements.

Certain aspects of the present invention may be found in the published and subsequently abandoned application PCT/US95/14549 "Universal Indicator for Physiological and Pathological Conditions" (by the inventors of the present invention); based on abandoned Israel application 111535. This application was abandoned because it did not contain sufficient disclosure for allowing the invention to be implemented, and because it became understood that significant additional research was necessary (by the inventors) in order to properly implement a valid embodiment. Nevertheless, the prior art references related therein-present partial teachings (of closely related problems) which are relevant to the present invention; and these references are:

Multinda J. H., Visser K. R. Estimation of blood pressure-related parameters by electrical impedance measurement. The Netherlands. J-Appl-Physiol. November 1992; 73(5):1946–57.

Ratzmann K. P. et al. Prevalence of peripheral and automic neuropathy in newly diagnosed type (non-insulin dependent) diabetes. J-Diabet-Compliacations. January–March 1991; 5(1):1–5.

Librenti M. C. et al Evaluation of an impedance measurement method for determining body composition in diabetes subjects and normal controls. Minerva-Endecrinol. January–March 1991; 16(1):27–30.

Wang L, Peterson R. P. Respratory effects on cardiac related impedance indices measured under voluntary cardio-respiratory synchronization. (VCRS) U.S. Med-Biol-Eng-Comput. September 1991; 29(5):505–10.

And Patents: Israel#71468 for A rheoplethsmographic device; and France#35484 for Apnea Monitoring method and apparatus.

Subsequent to the PCT application withdrawal, additional prior art citations have been found which further present relevant matter for understand the teachings of the present invention; and these citations (all being USA patents) are:

U.S. Pat. No. 3,835,840 Impedance plethysmography method and apparatus.

U.S. Pat. No. 3,949,736 Circuit for automatically deriving and measuring relative voltages associated with impedance components of a biological object.

U.S. Pat. No. 4,450,527 Noninvasive continuous cardiac output monitor.

U.S. Pat. No. 5,241,963 Method for detecting the onset and relative degree of atherosclerosis in humans.

U.S. Pat. No. 5,280,429 Method and apparatus for displaying multi-frequency bio-impedance.

U.S. Pat. No. 5,343,867 Method and apparatus for detecting the onset and relative degree of atherosclerosis in humans.

U.S. Pat. No. 5,421,344 Method and means of determining the health condition of a living creature.

U.S. Pat. No. 5,449,000 System for body impedance data acquisition utilizing segmental impedance & multiple frequency impedance.

U.S. Pat. No. 5,454,377 Method for measuring the myocardial electrical impedance spectrum.

U.S. Pat. No. 5,469,859 Non-invasive method and device for collecting measurements representing body activity and determining cardiorespiratory parameters of the human body based upon the measurements collected.

Accordingly, it would be considered a preferable result to allow prolonged impedance measurements outside of the clinical settings of the prior art, to provide a new avenue for collecting data on normal activity (human or otherwise), or to provide facile diagnostic monitoring options for patients presently restricted to remain in proximity to diagnostic professionals. Furthermore, it would be considered a preferable result to be able to disclose physiological events, especially those that may significantly effect other modalities of medical intervention.

SUMMARY OF THE INVENTION

The present invention relates to a non-invasive diagnostic physiological monitoring system for mammals, particulary humans, comprising:

(a.) at least two surface contact electrodes;

(b.) means for holding these electrodes in contact with an exterior surface of a mammal;

(c.) means for pairing these electrodes;

(d.) an electronic block coupled to at least one of the pairings wherein the block includes a transmitter for transmitting a predetermined electrical signal to a first pair of electrodes in the pairing, and a detector for detecting electrical impedance characteristics on the first pair of electrodes or on a second pair of electrodes in the pairing; and (e.) a signal processor coupled to the detector wherein the electrical impedance characteristics are divided into at least two groups by frequency.

A significant aspect of the present invention relates to data analysis performed at the signal processor (or at the electronic block). This analysis is particularly useful for extracting physiologically significant detail ("characteristics") from the impedance measurements. Characteristics may include measures that aid in the discernment of physiological indications pertaining to the state of the blood, veins, arteries, heart, or lungs.

On the one hand, the present invention measures multiple characteristics (e.g. on humans) in less than about 10 seconds (using an un-optimized prototype of the present system). This speed of measurement makes the system of the present invention a preferred diagnostic tool for emergency medical services personnel, since it can reveal measures of critical life-threatening internal injuries.

On the other hand, the present invention (being facile, portable, and unobtrusive) can be used to accumulate a broad collection of characteristics over a prolonged continuous measurement period of days. This may provide a patient profile (e.g. for humans) that is not otherwise obtainable.

Another interesting application of the present application relates to use for mammals (e.g. non-humans), such as cows or horses. This is a valuable tool for veterinarians, animal breeders, meat-packers, and other animal byproduct workers. For example, the present invention may provide an economically significant indication of a cow's suitability for Jewish ritual slaughter (wherein the internal organs must be intact) or of the cardiovascular capacity of a racehorse.

Normally use of the system of the present invention includes (methodologically) an initialization step of automatically normalizing the data values of the measured impedance according to five specific frequency separable data characteristics, the computing of a subsequent plurality of relative variations thereof, and the calculating of normalized diagnostic indices therefrom. The five specific data characteristics are the measured starting values for the constant composing impedance, the amplitude of the pulse wave, the frequency of the pulse wave, the amplitude of the breath wave, and the frequency of the breath wave.

The present invention also relates to a method for disclosing a physiological indication in a mammal, particularly a human. This method is especially useful for its convenience in disclosing of signal signature events in bio-impedance measurements. This disclosing is especially significant, for many discrete populations (or sub-populations) of subjects, in that the discernment of important physiological indications is provided thereby; or is otherwise probabilistically suggested.

Furthermore, it should be noted that the system of the present invention operates substantially according to the method of the present invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
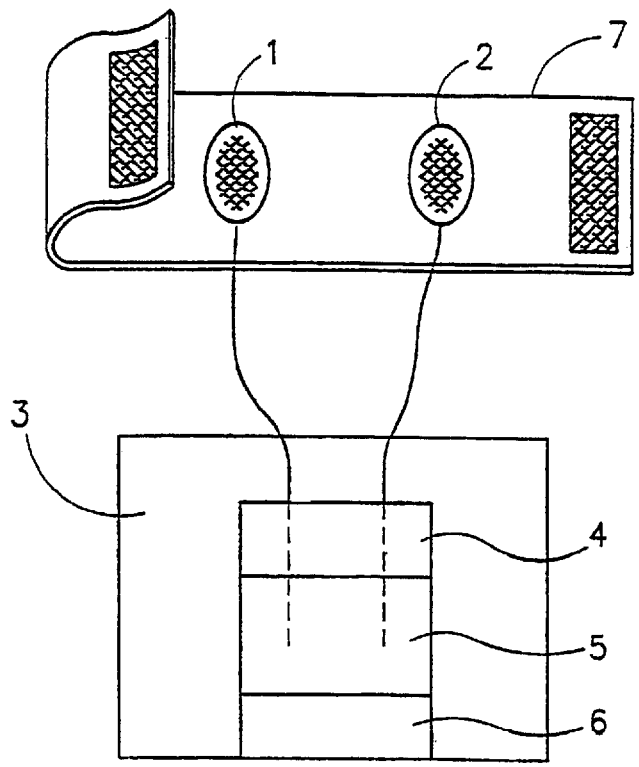
FIG. 1 is a schematic diagram of the system.

The present invention (see FIG. 1) relates to a non-invasive diagnostic physiological monitoring system for mammals, particularly humans, comprising: at least two surface contact electrodes (1) (2); means for holding these electrodes in contact with an exterior surface of a mammal; means for pairing the electrodes; an electronic block (3) coupled to at least one of the pairings wherein the block includes a transmitter (4) for transmitting a predetermined electrical signal to a first pair of electrodes in the pairing, and a detector (5) for detecting electrical impedance characteristics on the first pair of electrodes or on a second pair of electrodes in the pairing; and a signal processor (6) coupled to the detector wherein the electrical impedance characteristics are divided into at least two groups by frequency.

The means for holding the electrodes may be by using an adhesive member, by placing the electrodes between a limb and an elastic member wrapped there-around, etc. According to the preferred embodiment of the present invention the means for holding is an application member (7) having the at least two surface contact electrodes embedded therein. This application member is a wrist band, an arm band, a leg band, an ankle band, a belt, a head band, a neck band, a harness, or the like.

According to the preferred embodiment of the system of the present invention, the electrodes paired by the means for pairing are less than 15 cm distant from one another. This is a feature which is would not produce significant measurements in the absence of the signal processor. All of the known existing primitive single frequency group devices (in use today) require distances between paired electrodes of greater than 15 cm; which is equivalent to requiring more than one application member. Likewise according to the preferred embodiment of an application member, electrodes paired by the means for pairing are less than 15 cm distant from one another.

According to the preferred embodiment of the present invention, the surface contact electrodes are porous (e.g. of a partially sintered metallic aggregate, etc.). This provides greater skin contact and also results a better signal to noise ratio for the impedance measurements. Furthermore, according to the preferred embodiment of the present invention, the surface contact electrodes include a graphite surface portion; as a porous active-electrical contact-member of the electrode (e.g. in place of a partially sintered metallic aggregate).

According to the present invention there are two basic means for pairing electrodes; dynamic and static.

According to the preferred embodiment of the present invention, the means for pairing the electrodes is dynamically assigning, one electrode of the at least two surface contact electrodes to another electrode of the at least two surface contact electrodes, according to all possible pairing combinations or according to any subset thereof. For example, if there are 4 electrodes a b c and d, then dynamic pairing includes some or all of the following pairs: ab, ac, ad, bc, bd, cd, ba, ca, da, cb, db, dc. Use of dynamic pairing helps to guarantee that some pair of electrodes will be above larger blood vessels (veins or arteries)—without placement of the electrodes by a trained technician.

According to another significant embodiment of the present invention, the means for pairing the electrodes is by a static predetermined assignment of at least one electrode of the at least two surface contact electrodes to another electrode of the at least two surface contact electrodes. For example, if there are 4 electrodes a b c and d, then static pairing may simply be for the pairs ab and cd.

According to the preferred embodiment of the present invention the predetermined electrical signal transmitted by the transmitter is statically set to a value in the range of from about 15 kHz to about 90 kHz.

According to another embodiment of the present invention, which may be more suitable to the clinical setting, the predetermined electrical signal transmitted by the transmitter is discretely varied to include at least two predetermined frequency settings. For example, alternating between a static setting of 20 kHz for 15 seconds and a static setting of 75 kHz for 15 seconds. This use of multiple static settings may provide a second order refinement to the data resolution of the electronic block; and the higher resolution may allow the diagnostic differentiation of otherwise ambiguous physiological conditions. Thus according to a refinement of this embodiment, the signal processor operates on the signal detected, from each pairing of electrodes, independently for each frequency transmitted by the transmitter.

Certain specific frequency groups have been noted (using a fast Fourier transform algorithm FFT in the signal processor), and these are selected for the preferred embodiment of the present invention. These frequency groups are less than about 0.01 Hz, from about 0.01 Hz to about 0.4 Hz, and from about 0.4 Hz to about 5.0 Hz.

Frequency components of the characteristics of less than about 0.01 Hz reveal, essentially instantaneously, the base impedance. This discloses measures of blood volume (both absolute and as a function of time), blood impurities, blood gas (e.g. a bubble formation during decompression), blood sugar, blood viscosity, and quality of micro-circulation in capillary blood vessels; and may even be useful for forecasting the likelihood of myocardial infarction. This may also be useful in disclosing measures of growth of plasmic fibrinogen and hematokrit, the development of hyperholesteremia (the increase of lipoproteins by more than 180 mg/dl and of triglycerites by more than 150 mg/dl), skin vessels constriction, or the like.

Frequency components of the characteristics of from about 0.01 Hz to about 0.4 Hz reveal, essentially within about 12–15 seconds, the breath wave impedance. This discloses (according to its amplitude, frequency, and shape) such features as pulmonary edema, presence of blood in the lungs, and other more mundane physiological measures of lung function. Interestingly, this lung function measurement also detects if the user is awake or asleep—which in turn is of useful to know if the user must be awake (such as when driving a vehicle).

Frequency components of the characteristics of from about 0.4 Hz to about 5.0 Hz reveal, essentially within about 2–3 seconds, the pulse wave impedance. This discloses (according to its amplitude, frequency, and shape) the pulse, its regularity or irregularity (cardiac ventricular arrhythmia), etc. Also holosystolic noise, the result of mitral regurgiration due to ischemia of the cardiac papillary muscles, is expressed as the appearance of "noisy spikes" (high frequency components) located on the systolic part of the pulse component of the pulse wave.

According to the preferred embodiment of the present invention, the signal processor (or the electronic block) has characteristics divided into at least three groups by frequency; the base impedance, breath wave, and pulse wave.

According to a novel embodiment of the present invention, the electronic block includes a conversion of the characteristics into digital form. This is useful for data storage, data compression, and especially when the detector is remotely coupled to the signal processor (or the like) using a telecommunications intermediary.

Summarizing, the present invention include specific embodiments wherein one of the groups is for frequency components of the characteristics of, for example: (a) less than about 0.01 Hz; (b) from about 0.01 Hz to about 0.4 Hz; (c) from about 0.4 Hz to about 5.0 Hz; (d) having electrical impedance characteristics divided into at least three groups by frequency including at least one group from (a), (b), or (c); (e) having electrical impedance characteristics divided into three groups by frequency, wherein the first group is (a), the second group is (b), and the third group is (c); or (f) the like.

The present invention also relates to a method for disclosing a physiological indication in a mammal, particularly a human, comprising the steps of:

(a.) placing and holding at least two surface contact electrodes in contact with an exterior surface of a mammal;

(b.) pairing these electrodes;

(c.) transmitting a predetermined electrical signal to a first pair of electrodes in the pairing;

(d.) detecting electrical impedance characteristics on the first pair of electrodes or on a second pair of electrodes in the pairing;

(e.) signal processing the characteristics into at least one group by frequency;

(f.) monitoring for a signal signature event in a predetermined group of the at least one group; and (g.) disclosing the presence of the signal signature event, as a discerned physiological indication in the mammal.

According to the preferred embodiment of the method of the present invention, each electrode, of the at least two surface contact electrodes, is placed and held less than 30 cm away from every other electrode in the at least two surface contact electrodes.

According to the preferred embodiment of the method of the present invention, pairing the electrodes is dynamically assigned, within a predetermined set of possible pairings, until a pairing with an acceptably high signal to noise ratio is accepted by the monitoring.

According to the preferred embodiment of the method of the present invention signal processing of characteristics into at least one group by frequency includes a fast Fourier transform. According to another embodiment of the method of the present invention, signal processing of characteristics into at least one group by frequency includes a band pass filter.

Furthermore, according to the method of the present invention, an embodiment may be, and/or include, any of the following:

(a.) For disclosing the appearance of microtrombes in blood of the mammal, wherein the signal signature event being monitored for is an increasing of the base value, and the predetermined group is of frequency components less than about 0.01 Hz.

(b.) For a diabetic mammal, either disclosing an increase in the sugar level in blood of the mammal, or disclosing the appearance of carbohydrate metabolism disorder byproducts in blood of the mammal, wherein the signal signature event being monitored for is an increasing of the base value, and the predetermined group is of frequency components less than about 0.01 Hz.

(c.) For disclosing that the mammal is going to sleep, wherein the signal signature event being monitored for is an increase in amplitude and a decrease in frequency, and the predetermined group is of frequency components from about 0.01 Hz to about 0.4 Hz.

(d.) For a mammal during decompression, indicating the appearance of gas bubbles in blood of the mammal, wherein the signal signature event being monitored for is an increase in amplitude and an increase in frequency, and the predetermined group is of frequency components from about 0.01 Hz to about 0.4 Hz.

(e.) For a diabetic mammal, either disclosing an increase in the sugar level in blood of the mammal, or disclosing the appearance of carbohydrate metabolism disorder byproducts in blood of the mammal, wherein the signal signature event being monitored for is a decrease in amplitude and an increase in frequency, and the predetermined group is of frequency components from about 0.01 Hz to about 0.4 Hz.

Figure 2:
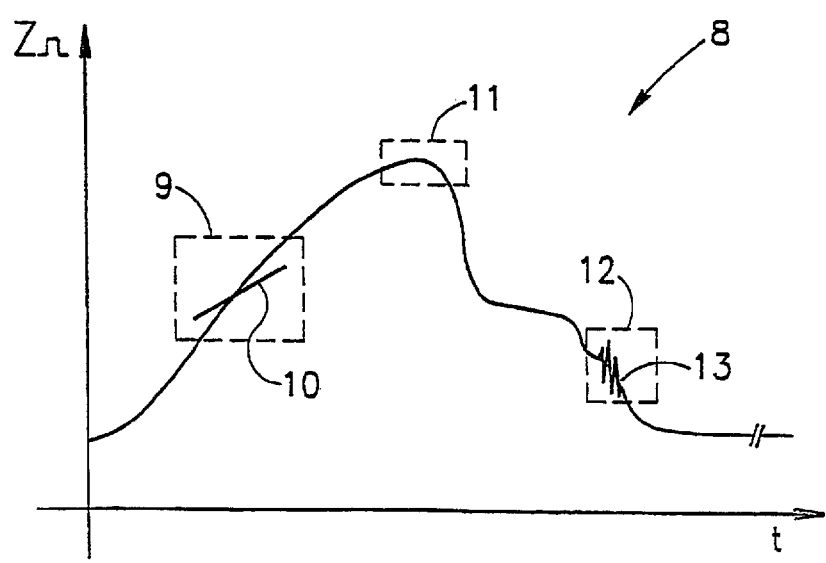
FIG. 2 is a schematic data graph from a subject for 0.4 Hz–5.0 Hz impedance measurement.

[Turning attention to a schematic data graph from a subject, for (0.4 Hz–5.0 Hz) impedance measurement group (FIG. 2), a section of the impedance measurement (8) is shown.]

(f.) For disclosing decreased elasticity in blood vessels (e.g. from cholesterol deposits) of the mammal, wherein the signal signature event being monitored for is a reduced slope (10) in the leading edge (9) of a measured impedance wave, and the predetermined group is of frequency components from about 0.4 Hz to about 5.0

(g.) For disclosing a transmission of microtrombes or of gas bubbles in blood vessels of the mammal, wherein the signal signature event being monitored for is an increase in the distribution of high frequency components (13) along the trailing edge (12) of a measured impedance wave, and the predetermined group is of frequency components from about 0.4 Hz to about 5.0 Hz.

There is also clinical significance associated with: a flat broad top versus a sharp spiked top-shape-region (11) of the impedance wave; the area of the wave under each section for each frequency group in isolation; comparison and correlation of area, shape, frequency, amplitude, and the like within a frequency group, between frequency groups, over time, etc.

Furthermore, according to the preferred embodiment of the method of the present invention, disclosing the presence of the signal signature event is by activating an alarm, or is by displaying a representation of the event on a data presentation screen, or is by storing data related to the event in a memory media.

It should be readily appreciated by those versed in the arts associated with bio-impedance measurements and interpretations, that the device and/or the method of the present invention may be extended to include many variations, which are substantially according to the scope and spirit of the present invention.

These variations relate to:
 (a.) Aspects of the diagnosis and/or the prognosis of specific physiological conditions.
 (b.) Aspects related to the monitoring and/or the treatment of these conditions [wherein the device and/or method of the present invention are incorporated].
 (c.) Passive or active validation of the fitness of individuals for activities having known (or knowable) constraints.

Examples of these variations include:
 (a.) Investigation of micro-circulation parameters of blood in extremities, diagnostics of the beginning of dysfunction of arterial and venous blood circulation (also thrombus in deep venous extremity), etc.
 (b.) Registration of biophysical parameters of blood, thrombus in the blood stream, indications of myocardial infarction or cerebral accident, indication of gas bubble formation in blood (caisson disease), presence of alcohol (or possibly narcotics) in blood, etc.
 (c.) Diagnostics of pneumotorex in all cases (e.g. accidents), latency oedema of lungs, etc.
 (d.) Control of type and dosage effectiveness of insulin during diabetes treatment, anticoagulant levels, etc.
 (e.) Checking of measures of alertness which have correlation measurable physiological indicators such as awareness for drivers, pilots, air traffic controllers, combat soldiers, watchmen, etc.

What is claimed is:

1. A non-invasive diagnostic physiological monitoring system for mammals, and adapted for humans, comprising:
 (a) one pair of surface contact electrodes;
 (b) an application member for holding said electrodes in contact with an exterior surface of a mammal, wherein said electrodes are embedded therein;
 (c) means for pairing said electrodes;
 (d) an electronic block coupled to said pair of electrodes wherein said block includes a transmitter for transmitting a predetermined electrical signal to said pair of electrodes, and a detector for detecting electrical impedance characteristics on said pair of electrodes; and
 (e) a signal processor coupled to the detector;
wherein
 said electrical impedance characteristics are divided into at least two groups by frequency, and
 a first one of the groups is for frequency components of the characteristics of less than about 0.01 Hz.

2. A non-invasive diagnostic physiological monitoring system for mammals, and adapted for humans, comprising:
 (a) one pair of surface contact electrodes;
 (b) an application member for holding said electrodes in contact with an exterior surface of a mammal, wherein said electrodes are embedded therein;
 (c) means for pairing said electrodes;
 (d) an electronic block coupled to said pair of electrodes wherein said block includes a transmitter for transmitting a predetermined electrical signal to said pair of electrodes, and a detector for detecting electrical impedance characteristics on said pair of electrodes; and
 (e) a signal processor coupled to the detector;
wherein
 said electrical impedance characteristics are divided into at least two groups by frequency, and
 one of the groups is for frequency components of the characteristics of from about 0.01 Hz to about 0.4 Hz.

3. A method for disclosing the appearance of microtrombes in the blood of a mammal, comprising:
 (a) placing and holding one pair of surface contact electrodes in contact with an exterior surface of a mammal, said electrodes being embedded in an application member;
 (b) transmitting a predetermined electrical signal to said pair of electrodes;
 (c) detecting electrical impedance characteristics on said pair of electrodes;
 (d) signal processing said characteristics into at least two groups by frequency;
 (e) monitoring for a signal signature event in a predetermined group of said at least two groups; and
 (f) disclosing the presence of said signal signature event, as a discerned physiological indication in the mammal; and
 wherein the signal signature event being monitored for is an increasing of the base value, and the predetermined group is of frequency components less than about 0.01 Hz.

4. A method for disclosing in a diabetic mammal, either an increase in the sugar level in blood of the mammal or the appearance of carbohydrate metabolism disorder byproducts in blood of the mammal; the method comprising:
 (a) placing and holding one pair of surface contact electrodes in contact with an exterior surface of a diabetic mammal, said electrodes being embedded in an application member;
 (b) transmitting a predetermined electrical signal to said pair of electrodes;

(c) detecting electrical impedance characteristics on said pair of electrodes;

(d) signal processing said characteristics into at least two groups by frequency;

(e) monitoring for a signal signature event in a predetermined group of said at least two groups; and (f) disclosing the presence of said signal signature event, as a discerned physiological indication in the diabetic mammal; and wherein the signal signature event being monitored for is an increasing of the base value, and the predetermined group is of frequency components less than about 0.01 Hz.

5. A method for disclosing a physiological indication in a mammal, during decompression, indicating the appearance of gas bubbles in blood of the mammal, the method comprising:

(a) placing and holding one pair of surface contact electrodes in contact with an exterior surface of a mammal, said electrodes being embedded in an application member;

(b) transmitting a predetermined electrical signal to said pair of electrodes;

(c) detecting electrical impedance characteristics on said pair of electrodes;

(d) signal processing said characteristics into at least two groups by frequency;

(e) monitoring for a signal signature event in a predetermined group of said at least two groups; and (f) disclosing the presence of said signal signature event, as a discerned physiological indication in the mammal, and wherein the signal signature event being monitored for is an increase in amplitude and an increase in frequency, and the predetermined group is of frequency components from about 0.01 Hz to about 0.4 Hz.

6. A method for disclosing a physiological indication in a diabetic mammal, said physiological indication being either an increase in the sugar level in blood of the mammal or the appearance of carbohydrate metabolism disorder byproducts in blood of the mammal; the method comprising:

(a) placing and holding one pair of surface contact electrodes in contact with an exterior surface of a diabetic mammal, said electrodes being embedded in an application member;

(b) transmitting a predetermined electrical signal to said pair of electrodes;

(c) detecting electrical impedance characteristics on said pair of electrodes;

(d) signal processing said characteristics into at least two groups by frequency;

(e) monitoring for a signal signature event in a predetermined group of said at least two groups; and (f) disclosing the presence of said signal signature event, as a discerned physiological indication in the diabetic mammal; and wherein the signal signature event being monitored for is a an increasing of the base value, and the predetermined group is of frequency components from about 0.01 Hz to about 0.4 Hz.

7. A method for disclosing decreased elasticity in blood vessels of a mammal, comprising:

(a) placing and holding one pair of surface contact electrodes in contact with an exterior surface of a mammal, said electrodes being embedded in an application member;

(b) transmitting a predetermined electrical signal to said pair of electrodes;

(c) detecting electrical impedance characteristics on said pair of electrodes;

(d) signal processing said characteristics into at least two groups by frequency;

(e) monitoring for a signal signature event in a predetermined group of said at least two groups; and (f) disclosing the presence of said signal signature event, as a discerned physiological indication in the mammal, and wherein the signal signature event being monitored for is a reduced slope in the leading edge of a measured impedance wave, and the predetermined group is of frequency components from about 0.4 Hz to about 5.0 Hz.

8. A method for disclosing a transmission of microtrombes or of gas bubbles in a blood vessel of a mammal comprising:

(a) placing and holding one pair of surface contact electrodes in contact with an exterior surface of a mammal, said electrodes being embedded in an application member;

(b) transmitting a predetermined electrical signal to said pair of electrodes;

(c) detecting electrical impedance characteristics on said pair of electrodes;

(d) signal processing said characteristics into at least two groups by frequency;

(e) monitoring for a signal signature event in a predetermined group of said at least two groups; and (f) disclosing the presence of said signal signature event, as a discerned physiological indication in the mammal; and wherein the signal signature event being monitored for is an increase in the distribution of high frequency components along a trailing edge of a measured impedance wave, and the predetermined group is of frequency components from about 0.4 Hz to about 5.0 Hz.

* * * * *

UNITED STATES PATENT AND TRADEMARK OFFICE
CERTIFICATE OF CORRECTION

PATENT NO. : 6,577,897 B1
DATED : June 10, 2003
INVENTOR(S) : Shurubura et al.

It is certified that error appears in the above-identified patent and that said Letters Patent is hereby corrected as shown below:

<u>Column 10,</u>
Line 55, insert the following claim:
9. The system according to claim 1 having electrical impedance characteristics divided into three groups by frequency, wherein the first said group is for said frequency components of the characteristics of less than about 0.01 Hz, a second said group is for frequency components of the characteristics of from about 0.01 Hz to about 0.4 Hz, and a third said group is for frequency components of the characteristics of from about 0.4 Hz to about 5.0 Hz.

Signed and Sealed this

Seventh Day of October, 2003

JAMES E. ROGAN
*Director of the United States Patent and Trademark Office*